United States Patent
Islam et al.

(10) Patent No.: US 11,951,649 B2
(45) Date of Patent: Apr. 9, 2024

(54) METHOD FOR PRODUCING COPPER CARBOXYLATE, A WOOD PRESERVATIVE COMPOSITION COMPRISING COPPER CARBOXYLATE, AND A WOOD PRODUCT PRODUCED THEREFROM

(71) Applicant: Koppers Performance Chemicals, Inc., Pittsburgh, PA (US)

(72) Inventors: Md Sayful Islam, Peachtree City, GA (US); Jun Zhang, Peachtree City, GA (US)

(73) Assignee: Koppers Performance Chemicals, Inc., Pittsburgh, PA (US)

( * ) Notice: Subject to any disclaimer, the term of this patent is extended or adjusted under 35 U.S.C. 154(b) by 0 days.

(21) Appl. No.: 17/854,196

(22) Filed: Jun. 30, 2022

(65) Prior Publication Data

US 2022/0332008 A1 Oct. 20, 2022

Related U.S. Application Data

(63) Continuation of application No. PCT/US2021/064126, filed on Dec. 17, 2021.

(60) Provisional application No. 63/143,396, filed on Jan. 29, 2021.

(51) Int. Cl.
*B27K 3/22* (2006.01)
*C07C 51/41* (2006.01)

(52) U.S. Cl.
CPC .............. *B27K 3/22* (2013.01); *C07C 51/412* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,071,862 | A | 2/1937 | Fisher | |
| 2,139,134 | A * | 12/1938 | Roon | C09F 9/00 106/310 |
| 2,584,041 | A * | 1/1952 | Nowak | C07C 51/412 556/139 |
| 2003/0053591 | A1 * | 3/2003 | Dunham | C08G 65/485 378/65 |
| 2014/0079806 | A1 | 3/2014 | Koop et al. | |
| 2018/0317486 | A1 * | 11/2018 | Zhang | B27K 3/0207 |

FOREIGN PATENT DOCUMENTS

| AU | 2016204205 A1 * | 1/2017 |
| CN | 106397178 A | 2/2017 |

OTHER PUBLICATIONS

MSDS for Mineral Spirits (Year: 2015).*
Sigma Aldrich Datasheet Naphthenic Acid (Year: 2023).*
Anonymous: "Copper naphthenate | Feb. 9, 1338", ChemicalBook, Jan. 1, 2017, XP055907233, Retrieved from the Internet: URL:https://www.chemicalbook.com/ChemicalProductProperty_EN_CB3205514.htm, 4 pages.
International Search Report and Written Opinion for International PCT Application No. PCT/US2021/064126, dated Apr. 12, 2022.

* cited by examiner

*Primary Examiner* — Robert T Butcher
(74) *Attorney, Agent, or Firm* — K&L Gates LLP

(57) ABSTRACT

A method for producing copper carboxylate, a wood preservative composition comprising copper carboxylate, and a wood product produced therefrom are provided. The method comprises combining a hydrocarbon solvent, a copper compound, and carboxylic acid and contacting the copper compound with the carboxylic acid in the presence of the hydrocarbon solvent to form a reaction product comprising copper carboxylate.

28 Claims, 5 Drawing Sheets

METHOD FOR PRODUCING COPPER CARBOXYLATE, A WOOD PRESERVATIVE COMPOSITION COMPRISING COPPER CARBOXYLATE, AND A WOOD PRODUCT PRODUCED THEREFROM

This application is a continuation of International Patent Application No. PCT/US2021/064126, filed Dec. 17, 2021, which claims the benefit of U.S. Provisional Application No. 63/143,396 filed Jan. 29, 2021, which are incorporated herein by reference.

FIELD

The present disclosure relates to a method for producing copper carboxylate, a wood preservative composition comprising copper carboxylate, and a wood product produced therefrom.

BACKGROUND

Copper carboxylates, such as, for example, copper naphthenate (e.g., CAS 1338-02-9) can be used as wood preservative. For example, copper naphthenate can be used for pressure treatments of wood products, such as, utility poles, railroad crossties/switch ties, cross arms, bridge timbers, fence posts, and lumber. There are challenges with producing copper carboxylate, and various disadvantages associated with copper carboxylate production processes.

SUMMARY

The present disclosure provides a method for producing copper carboxylate. The method comprises combining a hydrocarbon solvent, a copper compound, and carboxylic acid, and contacting the copper compound with the carboxylic acid in the presence of the hydrocarbon solvent to form a reaction product comprising copper carboxylate.

The present disclosure also provides a method for producing copper carboxylate, comprising combining a hydrocarbon solvent, a copper compound, and carboxylic acid, and contacting the copper compound with the carboxylic acid in the presence of the hydrocarbon solvent to form a reaction product comprising copper carboxylate.

The present disclosure also provides a wood product produced by treating the wood product with a wood preservative composition produced by combining a hydrocarbon solvent, a copper compound, and carboxylic acid and contacting the copper compound with the carboxylic acid in the presence of the hydrocarbon solvent to form a reaction product comprising copper carboxylate.

The present disclosure also provides a method for producing copper naphthenate. The method comprises combining a hydrocarbon solvent, a copper compound, and naphthenic acid, and contacting the copper compound with the naphthenic acid in the presence of the hydrocarbon solvent to form a reaction product comprising copper naphthenate.

The present disclosure also provides a method for producing copper naphthenate, comprising combining a hydrocarbon solvent, a copper compound, and naphthenic acid, and contacting the copper compound with the naphthenic acid in the presence of the hydrocarbon solvent to form a reaction product comprising copper naphthenate.

The present disclosure also provides a wood preservative composition comprising a copper carboxylate and penflufen.

The present disclosure also provides a wood product produced by treating the wood product with a wood preservative composition produced by combining a hydrocarbon solvent, a copper compound, and naphthenic acid and contacting the copper compound with the naphthenic acid in the presence of the hydrocarbon solvent to form a reaction product comprising copper naphthenate.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description of examples taken in conjunction with the accompanying drawings, wherein.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Certain exemplary aspects of the present disclosure will now be described to provide an overall understanding of the principles of the structure, function, manufacture, and use of the methods and systems disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various examples of the present disclosure is defined solely by the claims. The features illustrated or described in connection with one exemplary aspect may be combined with the features of other aspects. Such modifications and variations are intended to be included within the scope of the present disclosure.

Any references herein to "various examples," "some examples," "one example," "an example," similar references to "aspects," or the like, means that a particular feature, structure, or characteristic described in connection with the example is included in at least one example. Thus, appearances of the phrases "in various examples," "in some examples," "in one example," "in an example," similar references to "aspects," or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features, structures, or characteristics of one or more other examples without limitation. Such modifications and variations are intended to be included within the scope of the present examples.

There are various disadvantages associated with known copper carboxylate production processes, such as production of copper naphthenate. For example, production of copper naphthenate can comprise the addition of solid copper hydroxide to naphthenic acid which can result in a high initial viscosity (e.g., greater than 15,000 cps at 25 degrees Celsius) of the naphthenic acid and copper hydroxide slurry. The high viscosity can inhibit uniform agitation of the slurry that can result in a significant amount of solid sediment in a reaction vessel after the reaction. Additionally, typical copper naphthenate processes can comprise a relatively long reaction time and relatively low reaction rate/yield. The present disclosure provides a method for producing copper carboxylate that can improve one or more conditions or properties compared to known processes, such as, for example, reduced initial reaction viscosity, improved uniform agitation, reduced solid sediment, decreased reaction time, and/or increased reaction rate/yield.

Figure 1:
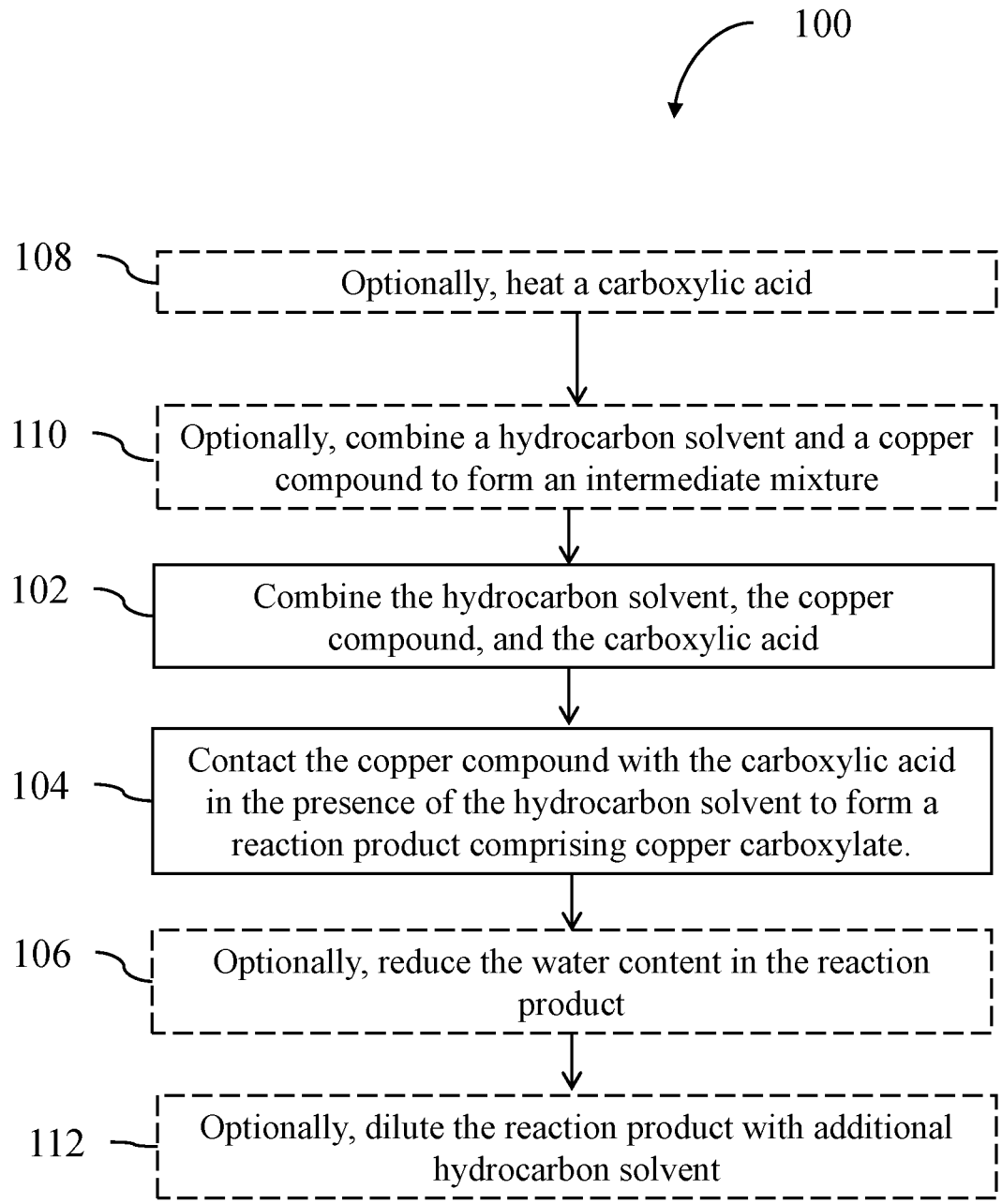
FIG. 1 is a flow chart illustrating an example of a method for producing copper carboxylate according to the present disclosure.

Referring to FIG. 1, flow chart 100 illustrates an example of a method of producing copper carboxylate according to the present disclosure. The method comprises a step 102 of combining a hydrocarbon solvent, a copper compound, and carboxylic acid to form a combined mixture. Combining the hydrocarbon solvent, the copper compound, and the carboxylic acid may be in any suitable manner or operation. For example, all or part of one of more of the hydrocarbon solvent, copper compound, and carboxylic acid materials can be combined in series or in various combinations in either batch or continuous operation to form the combined mixture.

The method further comprises a contacting step 104, wherein the copper compound can be contacted with the carboxylic acid in the presence of the hydrocarbon solvent to form a reaction product comprising copper carboxylate. A byproduct may be formed in the contacting step 104. Contacting 104 can be conducted under various suitable conditions and parameters that produce the reaction product comprising a carboxylate. Contacting 104 can comprise, for example, agitating. The general mechanism whereby copper compound can react with the carboxylic acid in the contacting step 104 is illustrated according to Scheme 1 below.

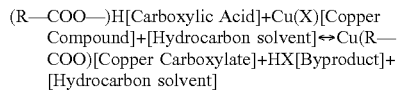

For example, where the copper compound comprises copper hydroxide, the reaction can proceed according to Scheme 2 below, with water as the byproduct.

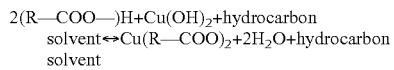

It has been found that when the copper compound is contacted with the carboxylic acid in the presence of the hydrocarbon solvent to form a reaction product comprising copper carboxylate, the hydrocarbon solvent can decrease the viscosity of the combined mixture of the copper compound and carboxylic acid thereby facilitating uniform agitation. For example, the hydrocarbon solvent can be inert to the reaction of the copper compound and the carboxylic acid. The hydrocarbon solvent can comprise distillate from petroleum feed stocks. In addition, the hydrocarbon solvent can comprise a mixture of linear, branched, and/or cyclic alkanes and/or aromatics. The hydrocarbon solvent can comprise one or more of various hydrocarbon solvents as defined by the American Wood Protection Association (AWPA) definition for Hydrocarbon Solvent as defined in AWPA standard HSA (e.g., Type A), HSC (e.g., Type C), HSF (e.g., Type F), HSG (e.g., Type G), and HSH (e.g., Type H). The hydrocarbon solvent can comprise diesel, fuel oil (e.g., #2 fuel oil (CAS #1338-24-5)), mineral spirits, pole-treating oil, a creosote-petroleum mixture, or a combination thereof. Furthermore, the hydrocarbon solvent can be suitable for use in a wood preservation composition for the treatment of a wood product against degradation due to termites and/or fungi. Therefore, the hydrocarbon solvent may not need to be removed from the reaction product prior to utilizing the reaction product as a wood preservation composition to treat a wood product.

As shown in Scheme 1 above, the production of copper carboxylate during the contacting step 104 can generate a byproduct. Removal of this byproduct, for example, through adjustment of process conditions during the reaction can increase the favorability of the production of copper carboxylate from the reactants and can result in a desirable product yield. For example, when the byproduct produced comprises water, the method of producing copper carboxylate 100 can optionally comprise a step 106 of reducing a water content in the reaction product. The water content of the reaction product can be reduced to no greater than 1 percent by weight of the reaction product, such as, for example, no greater than 0.5 percent by weight of the reaction product. At least a portion of reducing the water content 106 can occur simultaneously with at least a portion of contacting the copper compound with the carboxylic acid. For example, the water content can be reduced during at least a portion of the reaction of the copper compound and the carboxylic acid. In various examples, the water content can be reduced at least partially after the reaction is complete.

The water content in the reaction product can be reduced by various water removal methods, such as through adjustment of the temperature and pressure. For example, the water content in the reaction product can be reduced by heating the reaction product to a temperature of at least 100 degrees Celsius, reducing a pressure of the reaction product to less than atmospheric (i.e., 14.7 psia, 29.9 inHg), or a combination thereof. For example, the water content can be reduced by heating the reaction product to a temperature in a range of 100 degrees Celsius to 120 degrees Celsius or 100 degrees Celsius to 110 degrees Celsius. In various examples, reducing the pressure of the reaction product forms a vacuum of at least 0.1 inHg, such as, for example, at least 1 inHg or at least 2 inHg. For example, reducing the pressure of the reaction product can form a vacuum in a range of 0.1 inHg to 2.5 inHg.

The hydrocarbon solvent employed in methods of the present invention can comprise various hydrocarbon classes and chain lengths. The chain length and hydrocarbon classes of the hydrocarbon solvents suitable for use with the present disclosure can be selected to achieve a desired flash point and boiling point of the hydrocarbon solvent that are suitable for the production of copper carboxylate. For example, because water can be removed from the reaction product by heating the reaction product above the boiling point of water (i.e., 100 degrees Celsius), the boiling point of the hydrocarbon solvent can be selected to be greater than that of water such that the water can be separated from the reaction product by vaporization, such as, for example, distillation. For example, the hydrocarbon solvent can comprise a boiling point of at least 100 degrees Celsius, such as, for example, at least 110 degrees Celsius or at least 150 degrees Celsius. For example, the hydrocarbon solvent can comprise a boiling point in a range of 100 degrees Celsius to 300 degrees Celsius, such as, for example, 110 degrees Celsius to 250 degrees Celsius or 150 degrees Celsius to 250 degrees Celsius. A high boiling point can cause an undesirable viscosity in the combined mixture and/or reaction product; thus, the boiling point can be chosen to facilitate water evaporation while maintaining a desirable viscosity for the combined mixture and/or reaction product. In various examples, the hydrocarbon solvent can comprise a viscosity of no greater than 7 centistoke (cSt), no greater than 6 cSt, no greater than 5 cSt, no greater than 4 cSt, or no greater than 3.5 cSt, all measured at 25 degrees Celsius.

The reaction product can comprise at least 1% by weight of the hydrocarbon solvent, such as, for example, at least 5% by weight, at least 10% by weight, at least 15% by weight, at least 20% by weight, at least 25% by weight, or at least 30% by weight of the hydrocarbon solvent, based on the total weight of the combined mixture and/or reaction product. In various examples, the reaction product can comprise no greater than 80% by weight of the hydrocarbon solvent, such as, for example, no greater than 70% by weight, no greater than 60% by weight, no greater than 50% by weight, no greater than 40% by weight, or no greater than 35% by weight of the hydrocarbon solvent, based on the total weight of the combined mixture and/or reaction product. For example, the reaction product can comprise a range of 1% to 80% by weight of the hydrocarbon solvent, such as, for example, 5% to 60% by weight, 10% to 50% by weight, 20% to 40% by weight, or 25% to 35% by weight of the hydrocarbon solvent, based on the total weight of the combined mixture and/or reaction product Additionally, a low flash point can cause undesirable off-gassing, and a high flash point can cause a high viscosity in the combined mixture and/or reaction product. Thus, the flash point of the hydrocarbon solvent can be selected to limit off-gassing while maintaining a desirable viscosity in the combined mixture and/or the reaction product. The hydrocarbon solvent can comprise a flash point in a range of 25 degrees Celsius to 140 degrees Celsius, such as, for example, 30 degrees Celsius to 140 degrees Celsius, 45 degrees Celsius to 110 degrees Celsius, or 65 degrees Celsius to 100 degrees Celsius.

Table 1 lists the physical and chemical properties of various hydrocarbon solvents that may be used with the present disclosure.

TABLE 1

| Hydrocarbon Solvent | CAS | Flash Point (C.) | Boiling Point Range (C.) | Density (lb/gal) @15.6 C. | Kinemetric Viscosity (cSt) @25 C. |
|---|---|---|---|---|---|
| Exxsol D 40 | 64742-47-8 | 44 | 161-199 | 6.50 | 1.29 |
| Exxsol D 60 | 64742-47-8 | 64 | 190-211 | 6.60 | 1.69 |
| Exxsol D 80 | 64742-47-8 | 83 | 207-237 | 6.63 | 2.21 |
| Exxsol D 95 | 64742-47-8 | 96 | 225-256 | 6.68 | 2.78 |
| Exxsol D 110 | 64742-47-8 | 115 | 248-269 | 6.72 | 3.59 |
| Exxsol D 130 | 64742-46-7 | 137 | 279-311 | 6.93 | 6.38 |
| Varsol 1 | 8052-41-3 | 45 | 159-202 | 6.60 | 1.25 |
| Varsol 18 | 8052-41-3 | 44 | 160-202 | 6.54 | 1.31 |
| Varsol 60 | 64742-82-1 | 65 | 184-207 | 6.70 | 1.55 |
| Varsol 80 | 64742-81-0 | 80 | 204-241 | 6.84 | 2.11 |
| Varsol 110 | 64742-81-0 | 116 | 244-286 | 6.87 | 3.50 |
| Varsol 120 | 64742-81-0 | 120 | 256-297 | 7.06 | 4.67 |
| Varsol 140 | 64742-80-9 | 66 | 190-209 | 6.74 | 1.63 |
| Varsol 140 naphtha | 64742-47-8 | 65 | 189-208 | 6.69 | 1.55 |
| Aromatic 100 | 64742-95-6 | 46 | 160-171 | 7.28 | 0.95 |
| Aromatic 150 | 64742-94-5 | 65 | 184-204 | 7.49 | 1.32 |
| Aromatic 150 ND | 64742-94-5 | 64 | 183-194 | 7.38 | 1.24 |
| Aromatic 200 | 64742-94-5 | 107 | 234-284 | 8.23 | 3.00 |
| Aromatic 200 ND | 64742-94-5 | 111 | 242-285 | 8.26 | 3.12 |
| Diesel # 2 | 68476-34-6 | 58-76 | 154-366 | 6.84-7.34 | 1.90-3.32 |

The copper compound can comprise copper metal, copper (I) oxide, copper (II) oxide, copper hydroxide, copper carbonate, basic copper carbonate, copper oxychloride, or a combination thereof. For example, the copper compound can comprise copper hydroxide. If present, the copper hydroxide may be phosphor stabilized. The copper compound can comprise an elemental copper percentage of at least 55 percent by total weight of the copper compound, such as, for example, at least 61 percent or at least 62 percent by total weight of the copper compound. For example, the copper compound can comprise an elemental copper percentage in a range of 55 percent to 65 percent by total weight of the copper compound.

The copper compound can comprise a desirable particle size to facilitate the reaction of the copper compound with the carboxylic acid. For example, large particles may require more reaction time to complete the reaction compared to that of a finer particle. The copper compound can comprise a mean average particle size of the copper compound in a range of 0.05 μm to 500 μm, such as, for example, 0.05 μm to 100 μm. In various examples, the copper compound can be micronized. It has been found that a micronized copper compound can increase efficiency of the process, increase reaction speed, and facilitate ease of agitation.

Particle size can be determined by Stokes' Law relating to settling velocities of particles in a fluid, for example, with a Model LA 700 or a CAPA™ 700 sold by Horiba and Co. Ltd., which uses X-ray detection and bases calculations of size on Stokes' Law, to a size down to 0.2 microns. Particle sizes smaller than 0.2 microns can be determined by a dynamic light scattering method, preferably with a Coulter counter.

The carboxylic acid can comprise a single carboxylic acid or a mixture of two or more carboxylic acids. The carboxylic acid can be aliphatic, aromatic, or a mixture thereof. The carboxylic acid can be derived from a petroleum source (e.g., crude oil distillate), a non-petroleum source, or a combination thereof. For example, when the carboxylic acid comprises a mixture of two or more carboxylic acids, the mixture can comprise naphthenic acid and a carboxylic acid derived from a non-petroleum source. The concentration of the naphthenic acid can be in a range of 0.1% to 100% by weight based on the total weight of the mixture of two or more carboxylic acids and the carboxylic acid derived from non-petroleum source can be in a range of 0.1% to 99.9% by weight based on the total weight of the mixture. In various examples, when the carboxylic acid comprises a mixture of two or more carboxylic acids, the mixture can comprise no greater than 50% by weight of the carboxylic acid derived from a non-petroleum source based on the total weight of the mixture of the two or more carboxylic acids. The non-petroleum source of carboxylic acid can be an acid produced by a synthesis or derived from vegetable oils, animal oils, or other natural occurring sources such as, for example, soybean oil. The carboxylic acid derived from a non-petroleum source can have a general formula of R—COOH or R—$CO_2$H, where R— is an alkyl group, an alkenyl group, an aryl group, or other suitable group. In various examples, R can comprise a carbon backbone of at least 8 carbon atoms. For example, R can comprise a carbon backbone in a range of 8 carbon atoms to 40 carbon atoms, such as, for example, 8 carbon atoms to 20 carbon atoms or 9 carbon atoms to 20 carbon atoms. The R— group can be saturated or un-saturated group. For example, a carboxylic acid having a saturated R-group can comprise caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, behenic acid, lignoceric acid, cerotic acid, or a mixture thereof. A carboxylic acid having an unsaturated R-group can comprise myristoleic acid, palmitoleic acid, sapienic acid, oleic acid, elaidic acid, vaccenic acid, linoleic acid (e.g., α-linolenic acid), linoelaidic acid, arachidonic acid, eicosapentaenoic acid, erucic acid, docosahexaenoic acid, or a mixture thereof. In various examples, a carboxylic acid can comprise unsaturated monocarboxylic acids, fatty acids, amino acids, keto acids, aromatic carboxylic acids, dicarboxylic acids, tricarboxylic acids, alpha hydroxyl acids, beta hydroxy acids, omega hydroxy acids, divinylether fatty acids, or a mixture thereof. The pelargonic acid can be derived from vegetable oil with a carbon chain backbone length 9 and an acid value no greater than 355 mg/KOH/g. The arachidic acid can be derived from soybean oil.

The carboxylic acid derived from a petroleum source can comprise naphthenic acid. Naphthenic acid can comprise a mixture of different cycloaliphatic acids, such as, for example, cyclopentyl and cyclohexyl carboxylic acids recovered from the kerosene and diesel fraction during petroleum refining. Naphthenic acid can comprise a carboxylic acid with a carbon chain backbone length from 8 to 20, such as, for example 9 to 20. Naphthenic acid can comprise a molecular weight of at least 120 g/mol, such as, for example, in a range of 120 g/mol to well over 700 g/mol. Naphthenic acids are naphthenes (cycloparaffins) that contain carboxyl groups and are described by the general formula $C_nH_{2n-z}O_2$ in which n indicates the carbon number and z is zero or a positive integer that specifies the hydrogen deficiency resulting from ring formation, for example Z is 0, 2, 4, 6, or 8 for a homologous series. Z can be 0 for saturated acrylic acid, Z can be 2 for monocyclic naphthenic acid, Z can be 4 for bicyclic naphthenic acid, Z can be 6 for tricyclic naphthenic acid, and Z can be 8 for tetracyclic acids. For example, n may range from 8 to 20, such as, for example, 9 to 20. A suitable naphthenic acid can be derived from petroleum oil.

The copper carboxylate can be represented by the formula of Cu(R—COO)$_2$ where R—COO is the anion of a carboxylic acid. R can be an aklyl, akenyl, or aryl. In various examples, R can comprise a carbon backbone of at least 8 carbon atoms. For example, R can comprise a carbon backbone in a range of 8 carbon atoms to 40 carbon atoms, such as, for example, 8 carbon atoms to 20 carbon atoms or 9 carbon atoms to 20 carbon atoms. The copper carboxylate can comprise a single copper carboxylate or a mixture or two or more copper carboxylates. In various examples, the copper carboxylate comprises copper naphthenate.

Improper selection of carboxylic acids for making copper carboxylate can lead to undesirable properties of wood treated with the copper carboxylate. The carboxylic acid can comprise an acid value in a range of 100 mg KOH/g to 455 mg KOH/g, such as, for example, 100 mg KOH/g to 355 mg KOH/g, 150 mg KOH/g to 455 mg KOH/g, 150 mg KOH/g to 355 mg KOH/g, 180 mg KOH/g to 355 mg KOH/g, 200 mg KOH/g to 300 mg KOH/g, 225 mg KOH/g to 250 mg KOH/g, or 225 mg KOH/g to 245 mg KOH/g. The acid value can be measured according to AWPA Standard A13. Increasing the acid value may require the use of shorter carbon-chains in the carboxylic acid (e.g., less than 8) or a low-molecular-weight of carboxylic acid with a desired acid value, which can result in a high leach rate of copper from treated wood and more corrosivity of the treated wood towards metal fasteners.

The carboxylic acid can comprise a water content of less than 0.5 percent by total weight of the carboxylic acid. The carboxylic acid can comprise a viscosity of no greater than 1,500 cP at 25 degrees Celsius, such as, for example, no greater than 1,000 cP, no greater than 500 cP, or no greater than 250 cP, all at 25 degrees Celsius. For example, the carboxylic acid can comprise a viscosity in a range of 50 cP to 1500 cP at 25 degrees Celsius, such as, for example, 50 cP to 500 cP or 50 cP to 250 cP, all at 25 degrees Celsius. Viscosity can be measured with a Brookfield Viscometer using spindle number 2 and 3 at 25 degrees Celsius. Higher viscosities can cause fluid handling and mixing challenges during reaction and can increase the reaction time.

The molar ratio of carboxylic acid to elemental copper can be in a range of 1:1 to 5:1. The weight ratio of carboxylic acid to copper compound can be in a range of 1:1 to 20:1, such as, for example, 3:1 to 10:1 or 4.5:1 to 5:1. The weight ratio may change depending upon the copper compound used.

Referring again to FIG. 1, prior to combining of the hydrocarbon solvent, the copper compound, and the carboxylic acid, the method according to the present disclosure can comprise optional steps to improve reaction conditions or the product. For example, the method of the present invention may employ an optional heating step 108, wherein prior to combining of the hydrocarbon solvent, the copper compound, and the carboxylic acid the carboxylic acid may be heated to a temperature in a range of 30 degrees Celsius to 200 degrees Celsius, such as, for example, 50 degrees Celsius to 175 degrees Celsius, 50 degrees Celsius to 150 degrees Celsius, 50 degrees Celsius to 125 degrees Celsius, 30 degrees Celsius to 95 degrees Celsius, 50 degrees Celsius to 90 degrees Celsius, 55 degrees Celsius to 90 degrees Celsius, 65 degrees Celsius to 90 degrees Celsius, or 70 degrees Celsius to 85 degrees Celsius. The heating of the carboxylic acid can increase the reaction rate and/or yield of the copper carboxylate process.

Furthermore, it is contemplated that the hydrocarbon solvent and the copper compound can be combined to form an intermediate mixture prior to addition of the carboxylic acid, 110. Thereafter, the intermediate mixture can be combined with the carboxylic acid. Forming the intermediate mixture can enable formation of a uniform dispersion of the copper compound in the hydrocarbon solvent such that aggregation of the copper compound and/or copper carboxylate formed therefrom can be inhibited in order to reduce solid sediments in the reaction product. Copper carboxylate free of any solvent can exist as an amorphous, glassy solid. Therefore, if the copper carboxylate is not kept in a desirable size and/or inhibited from aggregation, the copper carboxylate may fall out of the solution and/or form undesirable solid sediments.

The intermediate mixture can be employed at a temperature in a range of 22 degrees Celsius to 125 degrees Celsius prior to combining with the carboxylic acid, such as, for example, 22 degrees Celsius to 95 degrees, 50 degrees Celsius to 125 degrees, 65 degrees Celsius to 90 degrees or 70 degrees Celsius to 85 degrees Celsius. Heating the intermediate mixture can increase the reaction rate and/or yield of the copper carboxylate process.

It is contemplated that the combined mixture may be formed at various viscosities. For example, the hydrocarbon solvent, the copper compound, and the carboxylic acid can be combined to form a combined mixture at a viscosity of no greater than 2,500 cP at 25 degrees Celsius, such as, for example, no greater than 2,000 cP, no greater than 1,000 cP, no greater than 500 cP, or no greater than 250 cP, all at 25 degrees Celsius.

The yield of the copper carboxylate from the reaction can be at least 90 percent within 2 hours of contacting the copper compound with the carboxylic acid, such as, for example, at least 95 percent, or at least 99 percent, all within 2 hours of contacting the copper compound with the carboxylic acid. The high yield within the 2 hour time frame can be achievable based on the selection of reaction conditions and reactants as discussed herein.

The reaction product can be diluted in an optional dilution step 112. It is contemplated that dilution can occur with additional hydrocarbon solvent, a biodiesel, and/or a vegetable oil. For example, the hydrocarbon solvent, biodiesel, and/or vegetable oil can be added to the copper compound at a level suitable to achieve a desired copper concentration. For example, a suitable copper concentration can be in a range of 2 percent by total weight of the reaction product to 12 percent by total weight of the reaction product, such as, for example, 6 percent by total weight of the reaction product to 10 percent by total weight of the reaction product, 8 percent by total weight of the reaction product to 10 percent by total weight of the reaction product, or 6 percent by total weight of the reaction product to 8 percent by total weight of the reaction product.

Biodiesel can comprise fatty acid esters produced from chemically reacting lipids (e.g., vegetable oil, animal fat) with an alcohol. Vegetable oil as used herein refers to compounds extracted from plants, which, for example, can be primarily triglyceride-based, and present as liquid, fatty waxy, or solid at room temperature. Vegetable oil can comprise saturated and unsaturated carbon-carbon double bonds. The vegetable oil can comprise linseed oil, coconut oil, corn oil, cottonseed oil, palm oil, canola oil, palm kernel oil, olive oil, peanut oil, rapeseed oil, safflower oil, sesame oil, soybean oil, sunflower oil, castor oil, tung oil, poppyseed oil, vernonia oil, almond oil, beech nut oil, Brazil nut oil, virgin oil, cashew oil, hazelnut oil, macadamia oil, mongongo nut oil (manketti oil), pecan oil, pine nut oil, pistachio oil, walnut oil, pumpkin seed oil, pracaxi oil, grape seed oil, rice bran oil, carapa oil, hempseed oil, or a combination thereof.

A wood preservative composition can be produced from the reaction product and/or dilute reaction product. The wood preservative composition can be used to treat a wood product against termites and/or fungi. For example, a method of treating a wood product to render it resistant to termites and/or fungal decay can comprise contacting the wood product with the wood preservative composition and drying the wood product. The wood products can comprise lumber, timbers, particle board, plywood, laminated veneer lumber (LVL), oriented strained board (OSB), utility poles, wood bridges, railroad crossties/switch ties, cross arms, bridge timbers, and fence posts. The wood product can comprise a wood species, such as, for example, southern pine, radiata pine, eucalyptus, Caribbean pine, ponderosa pine, red pine, eastern white pine, Scots pine, jack pine, lodgepole pine, spruce-pine-fir, Douglas fir, hem fir, eastern hemlock, western red cedar, maple, oak, or a combination thereof. In various examples, the wood preservative composition is solvent borne.

The wood preservative composition can also be used for supplemental or remedial treatment of wood products in service, such as, for example, utility poles and railroad ties. When used as a remedial preservative, the wood preservative composition can be in the form of paste or grease type of formulation, if desired, such that the formulation has an adhesive nature and is easy to apply to a desired location. When making a paste or grease type of formulation, 0.5 percent to about 30 percent by weight of a metal clay thickening agent, or a mixture of such thickening agents, can be used. The metal clay thickening agents include a fibrous structure type such as attapulgite clay and sepiolite clay, a non-crystal structure type such as allophone, and mixed layer structure type such as montmorillonite and kaolinite and the above layer structure types. The metal clay thickening agents can comprise attapulgite, dickite, saponite, montmorillonite, nacrite, kaolinite, anorthite, halloysite, meta-halloysite, chrysotile, lizardite, serpentine, antigorite, beidellite, stevensite, hectonite, smecnite, nacrite, sepiolite, montmorillonite, sauconite, nontronite, hectorite, vermiculite, illite, sericite, glauconite, roselite-montmorillonite, Bentone 38 (hectorite) and Bentone 34 (bentonite), chlorite-vermiculite, illite-montmorillonite, halloysite-montmorillonite, kaolinite-montmorillonite, or a combination thereof. The metal clay thickening agents can comprise exchangeable cations comprising aluminum ions, protons, sodium ions, potassium ions, calcium ions, magnesium ions, lithium ions, and the like. The metal clay thickening agents can comprise Attapulgite, hectorite, bentonite, montmorillonite, sauconite, smecnite, stevensite, beidellite, nontronite, saponite, vermiculite, nacrite, and sepiolite.

Additionally, a defoamer, a demulsifier, a biocide, or a combination thereof can be added to the reaction product and/or combined mixture. The demulsifier may be added to the reaction product in an amount ranging from 0.05 percent by weight to 0.5 percent by weight of the reaction product, such as, for example, 0.1 percent by weight to 0.25 percent by weight. Defoamer can be added to the combined mixture. Both silicone based and silicone-free defoamer can be used. For example, the defoamer can comprise BYK series defoamers (e.g., BYK-066N, 141, 1797, 1799, 1790, 1794, 1795); TEGO series defoamers (e.g., TEGO Foamex 840, 842, and 844, TEGO Airex 900, 990, and 931); Foam ban series defoamers (e.g., foam ban 130B, 149, 155, 169, 3633E, and 3920); Efka series defoamer (e.g., PB200, PB 2770, 2744, SI 2008); Xiameter series defoamers (e.g., Xiameter ACP 0001, 00080, 0544, 1000, 1400); and Dowsil series defoamers (e.g., 102F, ACP-2000, FS Antifoam 1266, BKP 63, FS 1265 Fluid 1000 cSt, and FBL 1165).

A wood preservation composition comprising copper carboxylate can form an emulsion in the presence of wood extractives, a trace amount of water, and/or particular treating conditions that can form a surface solid deposit onto the treated wood product such that the copper carboxylate cannot penetrate the wood product desirably. Therefore, a demulsifier can be added to the reaction product. The demulsifier can be added to the reaction product to achieve a concentration of demulsifier in a range of 50 ppm to 5000 ppm, such as, for example, 1000 ppm to 3000 ppm or 1750 ppm to 2250 ppm. For example, the demulsifier can be added to the reaction product to achieve a concentration of demulsifier of 2000 ppm or 120 ppm. The demulsifier can comprise Stepan series demulsifiers (e.g., Agent NE-3A, NE-3B, and NE-4); Kemelix series demulsifiers (e.g., D309, D310, D311, D322, D400, D501, D 510, 3515X, 3627X, 3697X, 3702X, 3750X, and 3754X); Demtrol series demulsifiers (e.g., 1030, 1040, 1130, 1135E, 2030, 2045, 4026, 6055, and 6237); and Reziflow series demulsifiers (e.g., 2110, 2215, 2130, 2140, 2205, 2210, 2300, 2305, 2600, 2605, 2720, and 2740).

A wood preservation composition comprising copper carboxylate through the reaction of copper compound and carboxylic acid can further comprise a biocide. The biocide can comprise a triazole, an imidazole, a pyrazole, a boron compound, a quaternary ammonium, an isothiazolone, a pyrethroid, or a combination thereof. Triazole and imidazole can comprise: 1-[[2-(2,4-dichlorophenyl)-1,3-dioxolan-2-yl]methyl]-1H-1,2,4-triazole (azaconazole), 1-[(2RS,4RS: 2RS,4SR)-4-bromo-2-(2,4-dichlorophenyl)tetrahydrofurfuryl]-1H-1,2,4-triazole (bromuconazole), (2RS,3RS;2RS, 3SR)-2-(4-chlorophenyl)-3-cyclopropyl-1-(1H-1,2,4-triazol-1-yl)butan-2-ol (Cyproconazole), (2RS,3RS)-1-(2,4-dichlorophenyl)-4,4-dimethyl-2-(1H-1,2,4-triazol-1-yl) pentan-3-ol (diclobutrazol), cis-trans-3-chloro-4-[4-methyl-2-(1H-1,2,4-triazol-1-ylmethyl)-1,3-dioxolan-2-yl]phenyl 4-chlorophenyl ether (difenoconazole), (E)-(RS)-1-(2,4-dichlorophenyl)-4,4-dimethyl-2-(1H-1,2,4-triazol-1-yl)pent-1-en-3-ol (diniconazole), (E)-(R)-1-(2,4-dichlorophenyl)-4, 4-dimethyl-2-(1H-1,2,4-triazol-1-yl)pent-1-en-3-ol (diniconazole-M), (2RS,3SR)-1-[3-(2-chlorophenyl)-2,3-epoxy-2-(4-fluorophenyl)propyl]-1H-1,2,4-triazole (epoxiconazole), (RS)-1-[2-(2,4-dichlorophenyl)-4-ethyl-1,3-dioxolan-2-ylmethyl]-1H-1,2,4-triazole (etaconazole), (RS)-4-(4-chlorophenyl)-2-phenyl-2-(1H-1,2,4-triazol-1-ylmethyl)butyronitrile (fenbuconazole), 3-(2,4-dichlorophenyl)-6-fluoro-2-(1H-1,2,4-triazol-1-yl) quinazolin-4(3H)-one (fluquinconazole), bis(4-fluorophenyl)(methyl)(1H-1,2,4-triazol-1-ylmethyl)silane (flusilazole), (RS)-2,4'-difluoro-α-(1H-1,2,4-triazol-1-ylmethyl)benzhydryl alcohol (flutriafol), (2RS,5RS;2RS,5SR)-5-(2,4-dichlorophenyl)tetrahydro-5-(1H-1,2,4-triazol-1-ylmethyl)-2-furyl 2,2,2-trifluoroethyl ether (furconazole), (2RS,5RS)-5-(2,4-dichlorophenyl)tetrahydro-5-(1H-1,2,4-triazol-1-ylmethyl)-2-furyl 2,2,2-trifluoroethyl ether (furconazole-cis), (RS)-2-(2,4-dichlorophenyl)-1-(1H-1,2,4-triazol-1-yl)hexan-2-ol (hexaconazole), 4-chlorobenzyl (EZ)—N-(2,4-dichlorophenyl)-2-(1H-1,2,4-triazol-1-yl) thioacetamidate (imibenconazole), (1RS,2SR,5RS;1RS, 2SR,5SR)-2-(4-chlorobenzyl)-5-isopropyl-1-(1H-1,2,4-triazol-1-ylmethyl)cyclopentanol (ipconazole), (1RS,5RS; 1RS,5SR)-5-(4-chlorobenzyl)-2,2-dimethyl-1-(1H-1,2,4-triazol-1-ylmethyl)cyclopentanol (metconazole), (RS)-2-(4-chlorophenyl)-2-(1H-1,2,4-triazol-1-ylmethyl)hexanenitrile (myclobutanil), (RS)-1-(2,4-dichloro-β-propylphenethyl)-1H-1,2,4-triazole(penconazole), cis-trans-1-[2-(2,4-dichlorophenyl)-4-propyl-1,3-dioxolan-2-ylmethyl]-1H-1,2,4-triazole (propiconazole), (RS)-2-[2-(1-chlorocyclopropyl)-3-(2-chlorophenyl)-2-hydroxypropyl]-2,4-dihydro-1,2,4-triazole-3-thione (prothioconazole), 3-(2,4-dichlorophenyl)-2-(1H-1,2,4-triazol-1-yl)-quinazolin-4(3H)-one (quinconazole), (RS)-2-(4-fluorophenyl)-1-(1H-1,2,4-triazol-1-yl)-3-(trimethylsilyl)propan-2-ol (simeconazole), (RS)-1-p-chlorophenyl-4,4-dimethyl-3-(1H-1,2,4-triazol-1-ylmethyl)pentan-3-ol (tebuconazole), propiconazole, (RS)-2-(2,4-dichlorophenyl)-3-(1H-1,2,4-triazol-1-yl)propyl 1,1, 2,2-tetrafluoroethyl ether (tetraconazole), (RS)-1-(4-chlorophenoxy)-3,3-dimethyl-1-(1H-1,2,4-triazol-1-yl) butan-2-one (triadimefon), (1RS,2RS; 1RS,2SR)-1-(4-chlorophenoxy)-3,3-dimethyl-1-(1H-1,2,4-triazol-1-yl) butan-2-ol (triadimenol), (RS)-(E)-5-(4-chlorobenzylidene)-2,2-dimethyl-1-(1H-1,2,4-triazol-1-ylmethyl)cyclopentanol (triticonazole), (E)-(RS)-1-(4-chlorophenyl)-4,4-dimethyl-2-(1H-1,2,4-triazol-1-yl)pent-1-en-3-ol (uniconazole), (E)-(S)-1-(4-chlorophenyl)-4,4-dimethyl-2-(1H-1,2,4-triazol-1-yl)pent-1-en-3-ol (uniconazole-P), 2-(2,4-difluorophenyl)-1-(1H-1,2,4-triazole-1-yl)-3-trimethylsilyl-2-propanol, or a combination thereof. Other azole compounds suitable as an organic biocide can comprise amisulbrom, bitertanol, fluotrimazole, triazbutil, climbazole, clotrimazole, imazalil, oxpoconazole, prochloraz, triflumizole, azaconazole, simeconazole, hexaconazole, or a combination thereof.

The pyrazole can comprise: benzovindiflupyr, bixafen, fenpyrazamine, fluxapyroxad, furametpyr, isopyrazam, oxathiapiprolin, penflufen, penthiopyrad, pydiflumetofen, pyraclostrobin, pyrametostrobin, pyraoxystrobin, rabenzazole, sedaxane, or a combination thereof.

The boron compound can comprise water-insoluble boron compounds, such as, for example, metal borate compounds (e.g., calcium borate, borate silicate, aluminum silicate borate hydroxide, silicate borate hydroxide fluoride, hydroxide silicate borate, sodium silicate borate, calcium silicate borate, aluminum borate, boron oxide, magnesium borate, iron borate, copper borate, and zinc borate (borax)).

The quaternary ammonium can comprise didecyldimethylammonium chloride; didecyldimethylammonium carbonate/bicarbonate; alkyldimethylbenzylammonium chloride; alkyldimethylbenzylammonium carbonate/bicarbonate; didodecyldimethylammonium chloride; didodecyldimethylammonium carbonate/bicarbonate; didodecyldimethylammonium propionate; N,N-didecyl-N-methyl-poly(oxyethyl) ammonium propionate, or a combination thereof.

The isothiazolone can comprise methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethylisothiazolinone, 4,5-Dichloro-2-n-octyl-3(2H)-isothiazolone, 1,2-benzisothiazolin-3-one, or a combination thereof.

The pyrethroid can comprise: acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute, silafluofen, or a combination thereof.

Other biocides that may be added to the reaction product comprise imidachloprid, fipronil, cyfluthrin, bifenthrin, permethrin, cypermethrin, chlorpyrifos, iodopropynyl butylcarbamate (IPBC), chlorothalonil, 2-(thiocyanatomethylthio)benzothiazole, alkoxylated diamines, carbendazim, or a combination thereof. Other biocides, such as fungicides, bactericides, and moldicides can also be added to the reaction product.

In various examples, penflufen may be added to the reaction product in a weight ratio, for example, of elemental copper:penflufen in a range of 5:1 to 250:1. The penflufen and copper carboxylate produce a synergistic efficacy against wood decay fungi, such as, for example, brown-rot decay fungi.

In certain examples, a solvent-borne wood preservative composition can comprise penflufen and copper carboxylate wherein the ratio of elemental copper:penflufen is in a range of 5:1 to 250:1. The solvent-borne wood preservative composition can be prepared by mixing the copper carboxylate, penflufen, and a carrier solvent. The carrier solvent can be a hydrocarbon solvent, a biodiesel, and/or a vegetable oil. The solvent-borne wood preservative composition can comprise at least 40% by weight of carrier solvent based on the total weight of the wood preservative composition, such as, for example, at least 60% by weight of carrier solvent, at least 80% by weight of carrier solvent, or at least 90% by weight of carrier solvent, all based on the total weight of the solvent-borne wood preservative composition. The concentration of the copper carboxylate in the wood preservative composition can be presence in an amount sufficient to achieve a desirable elemental copper concentration. For example, the solvent-borne wood preservative composition can comprise a range of 0.2% to 4% by weight of elemental copper based on the total weight of the solvent-borne wood preservative composition, such as, for example, 0.5% to 3% by weight of elemental copper, 0.8% to 2.5% by weight of elemental copper, or 1% to 2% by weight of elemental copper, all based on the total weight of the solvent-borne wood preservative composition. The solvent-borne wood preservative composition can comprise a range of 0.001% to 0.25% by weight of penflufen. Wood treated with the solvent-borne wood preservative composition can retain elemental copper and/or penflufen within the wood. For example, the elemental copper retention in the treated wood can be in a range of 0.5 $kg/m^3$ to 3.2 kilogram per cubic meter of wood ($kg/m^3$), such as, for example, 0.96 $kg/m^3$, 1.28 $kg/m^3$, or 2.1 $kg/m^3$. The penflufen retention in the treated wood can be in a range of 0.004 $kg/m^3$ to 0.2 $kg/m^3$, such as, for example, 0.008 $kg/m^3$, 0.012 $kg/m^3$, or 0.15 $kg/m^3$.

Figure 2:
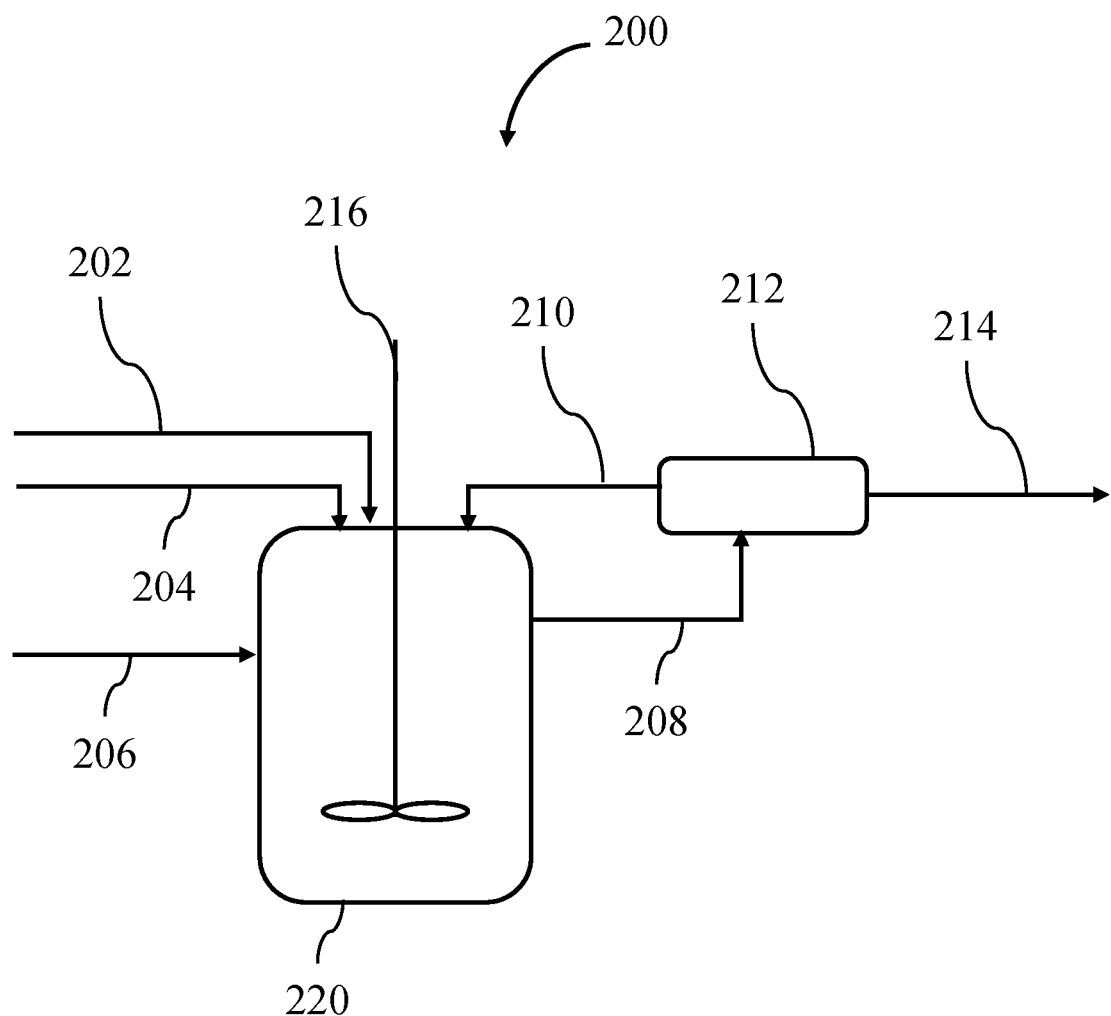
FIG. 2 is a block diagram illustrating an example of a system to produce copper carboxylate according to the present disclosure.

FIG. 2 illustrates an example of a system 200 to produce copper carboxylate according to the present disclosure. The system 200 can comprise a reaction vessel 220, a first inlet 202, a second inlet 204, a third inlet 206, a distillate line 208, a recirculation line 210, a condenser 212, a condensate line 214, and a stirrer 216. As illustrated, the system 200 can be operated in a batch process. It is understood that the system 200 could be modified to operate in a continuous process.

The first inlet 202 can be configured to receive the copper compound and transport the copper compound into the reaction vessel 220. The second inlet 204 can be configured to receive the hydrocarbon solvent and transport the hydrocarbon solvent into the reaction vessel 220. The third inlet 206 can be configured to receive carboxylic acid and transport the carboxylic acid into the reaction vessel 220. The first inlet 202, the second inlet 204, and the third inlet 206 can be configured such that their respective components can be preheated prior to delivery of that component into the reaction vessel 220.

As discussed above, it is contemplated that the copper compound from the first inlet 202 and the hydrocarbon solvent from the second inlet 204 can be combined to form an intermediate mixture. For example, the copper compound from the first inlet 202 and the hydrocarbon solvent from the second inlet 204 can be combined into a single stream (not shown) prior to delivery to the reaction vessel 220. In this form, the copper compound and the hydrocarbon solvent are premixed, such as by turbulent flow. In addition, it is contemplated that the reaction vessel 220 can be configured to receive the copper compound and the hydrocarbon solvent prior to the carboxylic acid such that the stirrer 216 can agitate the copper compound and hydrocarbon solvent to form the intermediate mixture with a uniform dispersion of the copper compound in the hydrocarbon solvent in the reaction vessel 220 prior to the addition of the carboxylic acid via the third inlet 206.

The stirrer 216 can be a paddle stirrer or other stirrer type suitable for agitating the reactants in the reaction vessel 220. The reaction vessel 220 can be configured with a heater to heat the reactants and/or reaction products. The reaction vessel 220 can be configured to reduce the pressure within the reaction vessel 220 to facilitate evaporation of water. The evaporated water can be transported through the distillate line 208 to the condenser 212. Condensed water can be removed through the condensate line 214. In various examples, a portion of the hydrocarbon solvent may vaporize, and the hydrocarbon solvent vapor can be condensed in the condenser 212 and recirculated back into the reaction vessel 220 through the recirculation line 210.

EXAMPLES

The present disclosure will be more fully understood by reference to the following examples, which provide illustrative non-limiting aspects of the invention. It is understood that the invention described in this specification is not necessarily limited to the examples described in this section.

Examples 1-3 illustrate three different copper naphthenate synthesis processes using a hydrocarbon solvent with flash point of 75 degrees Celsius, such as Diesel #2, as a diluent. Examples 4-9 demonstrate copper naphthenate synthesis processes with the same solvent as a diluent, a vacuum applied, and a demulsifier added in an efficient process. Examples 10-12 demonstrate copper naphthenate synthesis processes with lower flash point mineral spirits such as Varsol 1 as a diluent, a vacuum applied, and a demulsifier added in an efficient process. Examples 13-15 demonstrate copper naphthenate synthesis processes with higher flash point mineral spirits such as Varsol 110 as a diluent, a vacuum applied, and a demulsifier added in an efficient process. Examples 16-19 demonstrate copper carboxylate synthesis processes with Diesel #2, as diluent and a mixture of naphthenic acid and other carboxylic acid that are derived from non-petroleum oil sources. Examples 20-22 demonstrate copper carboxylate synthesis processes with Diesel #2 as diluent solvent and carboxylic acid that is derived from non-petroleum oil sources. The reactors in examples 1-22 were set up similar to the system 200 illustrated in FIG. 2

The naphthenic acid used in the examples described herein is product No. DNA 225 245 SR available from Unicore Specialty Mateirals Brugge, Blegium. The carboxylic acid derived from non-petroleum oil sources used herein is pelargonic and capric acid available at ACME-HARDESTY, Pennsylvania, USA.

Example 1

Figure 3A:
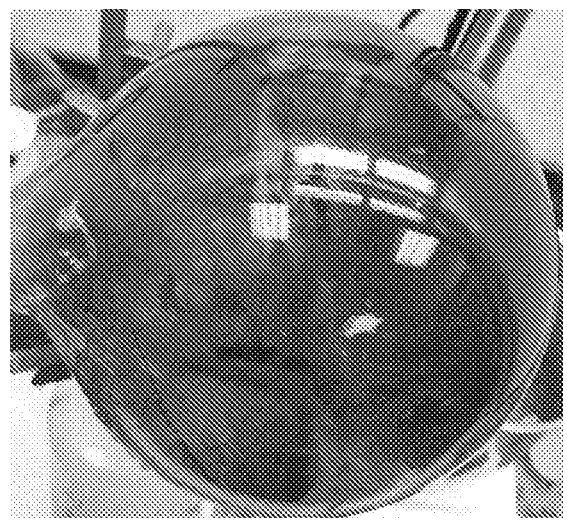
FIG. 3A is an image of the edge of the reactor of Example 1, provided herein, after the reaction was complete.
Figure 3B:
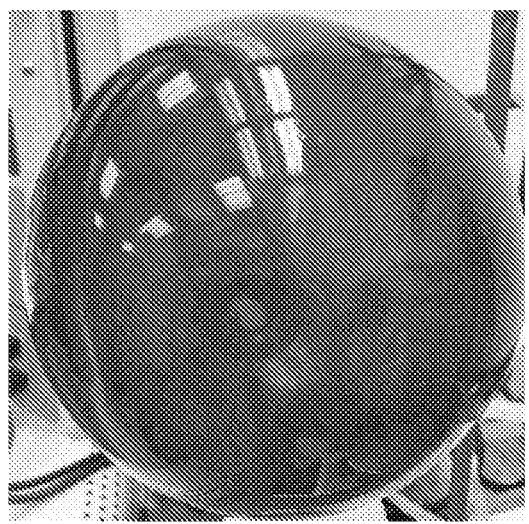
FIG. 3B is an image of the bottom of the reactor of Example 1 after the reaction was complete.

Copper naphthenate was synthesized by adding 264.88 grams (gm) of naphthenic acid into the reactor and then 55.13 g of copper hydroxide (64 percent copper basis) into the reactor while mixing to form a combined mixture. The combined mixture temperature was then set to 110 degrees Celsius while agitating. The reaction was completed in 120 minutes. Water generated during the reaction was removed and was measured to be at least 17.5 gm (some water vapor escaped into the atmosphere). The reaction is considered complete throughout the examples when minimal, if any, water condensate is exiting the reactor. The reactor contained less than 0.5% by weight of water after the reaction was complete and water removed. Finally, 140.89 gm of diesel #2 was added into the reactor to make a targeted 8 percent copper concentration in the final product. The initial copper hydroxide and naphthenic acid slurry had a very high viscosity (>15000 cP at 25 degrees Celsius), which was difficult to prepare a homogenous mixture from. Unreacted solid materials were observed around the reaction vessel edge and bottom after reaction completion even though the diesel #2 was added into the final product and agitated. The reactor after the completion of Example 1 is shown in FIGS. 3A-3B, where the unreacted solid materials can be seen.

Example 2

Figure 4A:
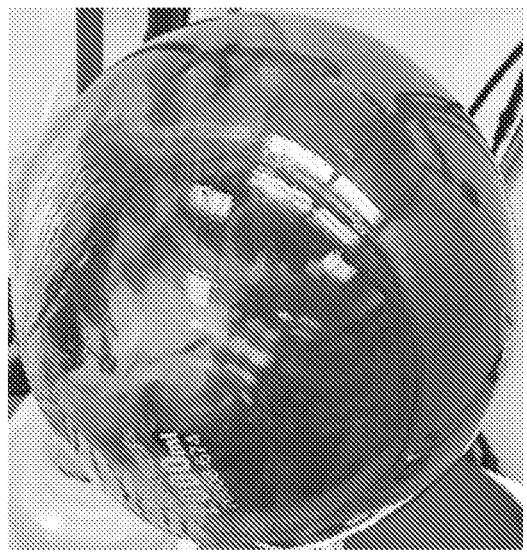
FIG. 4A is an image of the edge of the reactor of the reactor of Example 2, provided herein, after the reaction was complete.
Figure 4B:
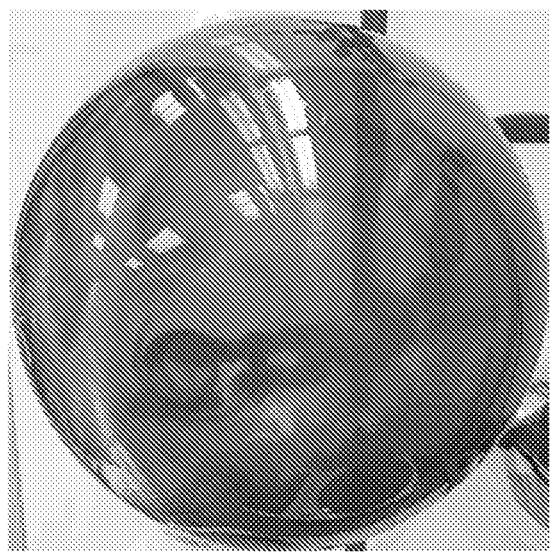
FIG. 4B is an image of the bottom of the reactor of Example 2 after the reaction was complete.

Copper naphthenate was synthesized by heating 91.88 g of diesel #2 at 75 degrees Celsius in the reactor. Then, 55.13 g of copper hydroxide (64 percent copper basis) was added into the reactor to form an intermediate mixture while continuously mixing and heating the intermediate mixture to 75 degrees Celsius. Then, 264.88 gm of naphthenic acid at room temperature (i.e., 22 degrees Celsius) was added to the intermediate mixture in the reactor to form a combined mixture, which had an initial viscosity of 350 cP at 25 degrees Celsius. The combined mixture temperature was then set to 110 degrees Celsius while agitating. Water generated during the reaction was removed and was measured to be at least 16.1 gm (some water vapor escaped into the atmosphere). The reactor contained less than 0.5% by weight of water after the reaction was complete and water removed. Diesel condensate was fed back into the reactor. The reaction was completed in 360 minutes. Finally, 49.01 gm of diesel #2 was added into the reactor to make targeted 8 percent copper concentration in the final product. Example 2 has an improved initial viscosity compared to Example 1 and provided a cleaner reaction product with minimal, if any, residual particles left in the reaction vessel after the reaction was completed. The reactor after the completion of Example 2 is shown in FIGS. 4A-4B, where minimal, if any, unreacted solid materials can be seen.

Example 3

Figure 5A:
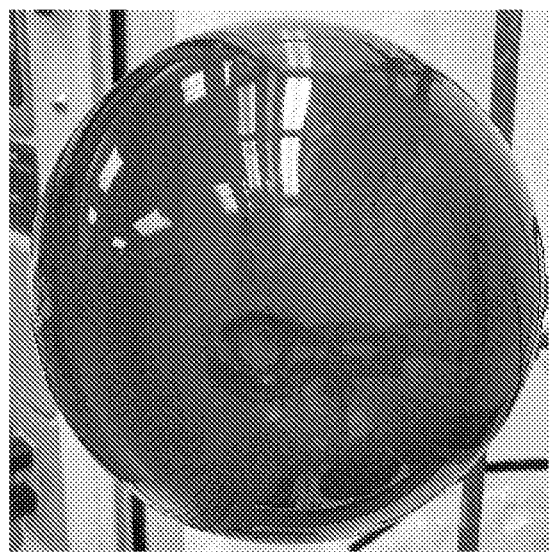
FIG. 5A is an image of the edge of the reactor of Example 3, provided herein, after the reaction was complete.
Figure 5B:
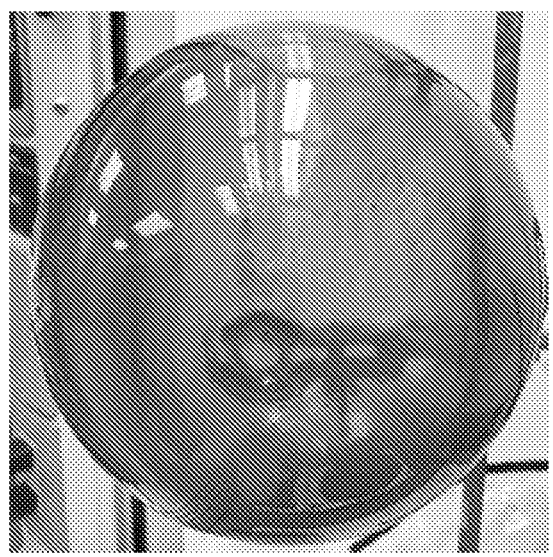
FIG. 5B is an image of the bottom of the reactor of Example 3 after the reaction was complete.

Copper naphthenate was synthesized by heating 91.88 g of diesel #2 at 75 degrees Celsius in the reactor. Then, 55.13 g of copper hydroxide (64 percent copper basis) was added into the reactor to form an intermediate mixture while continuously mixing and heating the intermediate mixture to 75 degrees Celsius. Then, 264.88 gm of naphthenic acid pre-heated at 70 degrees Celsius was added to the intermediate mixture in the reactor to form a combined mixture which had an initial viscosity of 350 cP at 25 degrees Celsius. The combined mixture temperature was then set to 110 degrees Celsius while agitating. Water generated during the reaction was removed and was measured to be at least 18 gm (some water vapor escaped into the atmosphere). The reactor contained less than 0.5% by weight of water after the reaction was complete and water removed. Diesel condensate was fed back to the reactor. The reaction was completed in 120 minutes. Finally, 49.01 gm of diesel #2 was added into the reactor to make targeted 8 percent copper concentration in the reaction product. Example 3 has an improved initial viscosity compared to Example 1 and provided a cleaner reaction product with minimal, if any, residual particles left in the reaction vessel after the reaction was completed. The reactor after the completion of Example 3 is shown in FIGS. 5A-5B, where minimal, if any, unreacted solid materials can be seen. Additionally, Example 3 had a fast reaction time compared to Example 2.

Example 4

Copper naphthenate was synthesized by heating 91.88 g of diesel #2 at 76 degrees Celsius in the reactor. Then, 55.13 g of copper hydroxide (64 percent copper basis) was added into the reactor to form an intermediate mixture while continuously mixing and heating the intermediate mixture to 78 degrees Celsius. Then, 264.88 gm of naphthenic acid pre-heated at 70 degrees Celsius was added to the intermediate mixture to form a combined mixture. The combined mixture temperature was then set to 110 Celsius while agitating. Water generated during the reaction was removed and was measured to be at least 17.63 gm (some water vapor escaped into the atmosphere). The reactor contained less than 0.5% by weight of water after the reaction was complete and water removed. Diesel condensate was fed back into the reactor. The reaction was completed in 120 minutes. Finally, 49.01 gm of diesel #2 and 0.46 g of demulsifier were added into the reactor to make a targeted 8 percent copper concentration in the reaction product. Example 4 had a suitable initial viscosity of less than 400 cP and provided a clean reaction product with minimal, if any, residual solid materials left in the reactor after reaction completion.

Example 5

Copper naphthenate was synthesized by heating 91.88 g of diesel #2 at 75 degrees in the reactor. Then, 55.13 g of copper hydroxide (64 percent copper basis) was added into the reactor to form an intermediate mixture while continuously mixing and heating the intermediate mixture to 79.6 degrees Celsius. Then, 264.88 gm of naphthenic acid pre-heated at 83.6 degrees Celsius was added to the intermediate mixture to form a combined mixture. The combined mixture temperature was then set to 110 degrees Celsius while agitating. Water generated during the reaction was removed and was measured to be at least 18 gm (some water vapor escaped into the atmosphere). The reactor contained less than 0.5% by weight of water after the reaction was complete and water removed. Diesel condensate was fed back into the reactor. The reaction was completed in 120 minutes. Finally, 49.01 gm of diesel #2 and 0.46 g of demulsifier was added into the reactor to make targeted 8 percent copper concentration in the reaction product. Example 5 had a suitable initial viscosity of less than 400 cP and provided a clean reaction product with minimal, if any, residual solid materials left in the reactor after reaction completion.

Example 6

Copper naphthenate was synthesized by heating 91.88 g of diesel #2 at 79.2 degrees Celsius in the reactor. Then, 55.13 g of copper hydroxide (64 percent copper basis) was added into the reactor to form an intermediate mixture while continuously mixing and heating the intermediate mixture to 84.4 degrees Celsius. Then, 264.88 gm of naphthenic acid preheated at 73.1 degrees Celsius was added to the intermediate mixture to form a combined mixture. The combined mixture temperature was set to 110 degrees Celsius while agitating. Water generated during the reaction was removed and was measured to be at least 16.40 gm (some water vapor escaped into the atmosphere). The reactor contained less than 0.5% by weight of water after the reaction was complete and water removed. Diesel condensate was fed back to the reactor. The reaction was completed in 117 minutes. Finally, 49.01 gm of diesel #2 and 0.46 g of demulsifier were added into the reactor to make a targeted 8 percent copper concentration in the reaction product. Example 6 had a suitable initial viscosity of less than 400 cP and provided a clean reaction product with minimal, if any, residual solid materials left in the reactor after reaction completion.

Example 7

Copper naphthenate was synthesized by heating 91.88 g of diesel #2 at 70 degrees Celsius in the reactor. Then, 55.13 g of copper hydroxide (64 percent copper basis) was added into the reactor to form an intermediate mixture while continuously mixing and heating the intermediate mixture to 70 degrees Celsius. Then, 264.88 gm of naphthenic acid at room temperature (22 degrees Celsius) was added to the intermediate mixture to form a combined mixture. The combined mixture temperature was then set to 110 Celsius while agitating, and a low vacuum <0.1 cm Hg was applied to the reactor. Water generated during the reaction was removed and was measured to be at least 14.82 gm (some water vapor escaped into the atmosphere). It is believed that more water is present in the reactor than if the naphthenic acid was preheated. Diesel condensate was fed back into the reactor. The reaction was completed in 45 minutes. Finally, 49.01 gm of diesel #2 and 0.46 g of demulsifier were added into the reactor to make a targeted 8 percent copper concentration in the reaction product. Example 7 had a suitable initial viscosity of less than 400 cP and provided a clean reaction product with minimal, if any, residual solid materials left in the reactor after reaction completion.

Example 8

Copper naphthenate was synthesized by heating 91.88 g of diesel #2 at 70 degrees in the reactor. Then, 55.13 g of copper hydroxide (64 percent copper basis) was added into the reactor to form an intermediate mixture while continuously mixing and heating the intermediate mixture to 73.7 degrees Celsius. Then, 264.88 gm of naphthenic acid pre-heated at 75 degrees Celsius was added to the intermediate mixture to form a combined mixture. The combined mixture temperature was then set to 110 Celsius while agitating, and a low vacuum <0.1 cm Hg was applied to the reactor. Water generated during the reaction was removed and was measured to be at least 14.42 gm (some water vapor escaped into the atmosphere). The reactor contained less than 0.5% by weight of water after the reaction was complete and water removed. Diesel condensate was fed back into the reactor. The reaction was completed in 35 minutes. Finally, 49.01 gm of diesel #2 was added into the reactor to make a targeted 8 percent copper concentration in the reaction product. Example 8 had a suitable initial viscosity and provided a clean reaction product with minimal, if any, residual solid materials left in the reactor after reaction completion.

Example 9

Copper naphthenate was synthesized by heating 91.88 g of diesel #2 at 75 degrees Celsius in the reactor. Then, 55.13 g of copper hydroxide (64 percent copper basis) was added into the reactor to form an intermediate mixture while continuously mixing and heating the intermediate mixture to 75 degrees Celsius. Then, 264.88 gm of naphthenic acid pre-heated at 76 degrees Celsius was added to the intermediate mixture to form a combined mixture. The combined mixture temperature was then set to 110 degrees Celsius while agitating, and a low vacuum <0.1 cm Hg was applied to the reactor. Water generated during the reaction was removed and was measured to be at least 14.94 gm (some water vapor escaped into the atmosphere). The reactor contained less than 0.5% by weight of water after the reaction was complete and water removed. Diesel condensate was fed back into the reactor. The reaction was completed in 35 minutes. Finally, 49.01 gm of diesel #2 and 0.46 g of demulsifier were added into the reactor to make a targeted 8 percent copper concentration in the reaction product. Example 9 had a suitable initial viscosity of less than 400 cP and provided a clean reaction product with minimal, if any, residual solid materials left in the reactor after reaction completion.

Example 10

Copper naphthenate was synthesized by heating 59.42 g of Varsol 1 at 70 degrees Celsius in the reactor. Then, 35.90 g of copper hydroxide (64 percent copper basis) was added into the reactor to form an intermediate mixture while continuously mixing and heating the intermediate mixture to 70 degrees Celsius. Then, 172.44 gm of naphthenic acid pre-heated at 76.5 degrees Celsius was added to the intermediate mixture to form a combined mixture. The combined mixture temperature was then set to 110 degrees Celsius while agitating, and a low vacuum <0.1 cm Hg was applied to the reactor. Water generated during the reaction was removed and was measured to be at least 6.4 gm (some water vapor escaped into the atmosphere). The reactor contained less than 0.5% by weight of water after the reaction was complete and water removed. Varsol 1 condensate was fed back into the reactor. The reaction was completed in 36 minutes. Finally, 31.99 gm of Varsol 1 was added into the reactor to make a targeted 8 percent copper concentration in the reaction product. Example 10 had a suitable initial viscosity of less than 400 cP and provided a clean reaction product with minimal, if any, residual solid materials left in the reactor after reaction completion.

Example 11

Copper naphthenate was synthesized by heating 108.93 g of Varsol 1 at 70 degrees Celsius to the reactor. Then, 65.80 g of copper hydroxide (64 percent copper basis) was added into the reactor to form an intermediate mixture while continuously mixing and heating the intermediate mixture to 71 degrees Celsius. Then, 316.09 gm of naphthenic acid pre-heated at 73 degrees Celsius was added to the intermediate mixture to form a combined mixture. The combined mixture temperature was then set to 110 degrees Celsius while agitating, and a low vacuum <0.1 cm Hg was applied to the reactor. Water generated during the reaction was removed and was measured to be at least 15.08 gm (some water vapor escaped into the atmosphere). The reactor contained less than 0.5% by weight of water after the reaction was complete and water removed. Varsol 1 condensate was fed back into the reactor. The reaction was completed in 35 minutes. Finally, 58.65 gm of Varsol 1 and 0.55 g of demulsifier were added into the reactor to make a targeted 8 percent copper concentration in the reaction product. Example 11 had a suitable initial viscosity of less than 400 cP and provided a clean reaction product with minimal, if any, residual solid materials left in the reactor after reaction completion.

Example 12

Copper naphthenate was synthesized by heating 91.28 g of Varsol 1 at 70 degrees Celsius in the reactor. Then, 55.12 g of copper hydroxide (64 percent copper basis) was added into the reactor to form an intermediate mixture while continuously mixing and heating the intermediate mixture to 71 degrees Celsius. Then, 264.88 gm of naphthenic acid pre-heated at 82 degrees Celsius was added to the intermediate mixture to form a combined mixture. The combined mixture temperature was then set to 110 degrees Celsius while agitating, and a low vacuum <0.1 cm Hg was applied to the reactor. Water generated during the reaction was removed and was measured to be at least 12.58 gm (some water vapor escaped into the atmosphere). The reactor contained less than 0.5% by weight of water after the reaction was complete and water removed. Varsol 1 condensate was fed back into the reactor. The reaction was completed in 35 minutes. Finally, 49.16 gm of Varsol 1 and 0.46 g of demulsifier were added into the reactor to make a targeted 8 percent copper concentration in the reaction product. Example 12 had a suitable initial viscosity of less than 400 cP and provided a clean reaction product with minimal, if any, residual solid materials left in the reactor after reaction completion.

Example 13

Copper naphthenate was synthesized by heating 91.28 g of Varsol 110 at 72 degrees Celsius in the reactor. Then, 55.12 g of copper hydroxide (64 percent copper basis) was added into the reactor to form an intermediate mixture while continuously mixing and heating the intermediate mixture to 74.2 degrees Celsius. Then, 264.88 gm of naphthenic acid pre-heated at 73 degrees Celsius was added to the intermediate mixture to form a combined mixture. The combined mixture temperature was then set to 110 degrees Celsius while agitating, and a low vacuum <0.1 cm Hg was applied to the reactor. Water generated during the reaction was removed and was measured to be at least 17.30 gm (some water vapor escaped into the atmosphere). The reactor contained less than 0.5% by weight of water after the reaction was complete and water removed. Varsol 110 condensate was fed back into the reactor. The reaction was completed in 35 minutes. Finally, 49.16 gm of Varsol 110 was added into the reactor to make a targeted 8 percent copper concentration in the reaction product. Example 13 had a suitable initial viscosity of less than 400 cP and provided a clean reaction product with minimal, if any, residual solid materials left in the reactor after reaction completion.

Example 14

Copper naphthenate was synthesized by heating 91.28 g of Varsol 110 at 70.4 degrees Celsius in the reactor. Then, 55.12 g of copper hydroxide (64 percent copper basis) was added into the reactor to form an intermediate mixture while continuously mixing and heating the intermediate mixture to 70.8 degrees Celsius. Then, 264.88 gm of naphthenic acid pre-heated at 70.8 degrees Celsius was added to the intermediate mixture to form a combined mixture. The combined mixture temperature was set to 110 degrees Celsius while agitating, and a low vacuum <0.1 cm Hg was applied to the reactor. Water generated during the reaction was removed and was measured to be at least 15.20 gm (some water vapor escaped into the atmosphere). The reactor contained less than 0.5% by weight of water after the reaction was complete and water removed. Varsol 110 condensate was fed back into the reactor. The reaction was completed in 35 minutes. Finally, 49.16 gm of Varsol 110 and 0.46 g of demulsifier was added into the reactor to make a targeted 8 percent copper concentration in the reaction product. Example 14 had a suitable initial viscosity of less than 400 cP and provided a clean reaction product with minimal, if any, residual solid materials left in the reactor after reaction completion.

Example 15

Copper naphthenate was synthesized by heating 91.28 g of Varsol 110 at 72 degrees Celsius in the reactor. Then, 55.12 g of copper hydroxide (64 percent copper basis) was added into the reactor to form an intermediate mixture while continuously mixing and heating the intermediate mixture to 75 degrees Celsius. Then, 264.88 gm of naphthenic acid pre-heated at 72 degrees Celsius was added to the intermediate mixture to form a combined mixture. The combined mixture temperature was then set to 110 degrees Celsius while agitating, and a low vacuum <0.1 cm Hg was applied to the reactor. Water generated during the reaction was removed and was measured to be at least 17.00 gm (some water vapor escaped into the atmosphere). The reactor contained less than 0.5% by weight of water after the reaction was complete and water removed. Varsol 110 condensate was fed back into the reactor. The reaction was completed in 35 minutes. Finally, 49.16 gm of Varsol 110 and 0.46 g of demulsifier were added into the reactor to make a targeted 8 percent copper concentration in the reaction product. Example 15 had a suitable initial viscosity of less than 400 cP and provided a clean reaction product with minimal, if any, residual solid materials left in the reactor after reaction completion.

Example 16

Copper carboxylate was synthesized by heating 91.88 g of diesel #2 at 75 degrees Celsius in the reactor. Then, 55.13 g of copper hydroxide (64 percent copper basis) was added into the reactor to form an intermediate mixture while continuously mixing and heating the intermediate mixture to 75 degrees Celsius. Then, 238.39 gm of naphthenic acid and 26.49 g of pelargonic acid mixture pre-heated at 76 degrees Celsius was added to the intermediate mixture to form a combined mixture. The combined mixture temperature was then set to 110 degrees Celsius while agitating, and a low vacuum <0.1 cm Hg was applied to the reactor. Water generated during the reaction was removed and measured to be at least 14.94 gm (some water vapor escapes into the atmosphere). The reactor contained less than 0.5% by weight of water after the reaction was complete and water removed. Diesel condensate was fed back into the reactor. The reaction was completed in 35 minutes. Finally, 49.01 gm of diesel #2 and 0.46 g of demulsifier were added into the reactor to make a targeted 8 percent copper concentration in the reaction product. Example 16 had a suitable initial viscosity of less than 400 cP and provided a clean reaction product with minimal, if any, residual solid materials left in the reactor after reaction completion.

Example 17

Copper carboxylate was synthesized by heating 91.88 g of diesel #2 at 75 degrees Celsius in the reactor. Then, 55.13 g of copper hydroxide (64 percent copper basis) was added into the reactor to form an intermediate mixture while continuously mixing and heating the intermediate mixture to 75 degrees Celsius. Then, 185.42 gm of naphthenic acid and 79.46 g of pelargonic acid mixture pre-heated at 76 degrees Celsius was added to the intermediate mixture to form a combined mixture. The combined mixture temperature was then set to 110 degrees Celsius while agitating, and a low vacuum <0.1 cm Hg was applied to the reactor. Water generated during the reaction was removed and measured to be at least 14.94 gm (some water vapor escapes into the atmosphere). The reactor contained less than 0.5% by weight of water after the reaction was complete and water removed. Diesel condensate was fed back into the reactor. The reaction was completed in 35 minutes. Finally, 49.01 gm of diesel #2 and 0.46 g of demulsifier were added into the reactor to make a targeted 8 percent copper concentration in the reaction product. Example 17 had a suitable initial viscosity of less than 400 cP and provided a clean reaction product with minimal, if any, residual solid materials left in the reactor after reaction completion.

Prophetic Example 18

Copper carboxylate can be synthesized by heating 91.88 g of diesel #2 at 75 degrees Celsius in the reactor. Then, 55.13 g of copper hydroxide (64 percent copper basis) can be added into the reactor to form an intermediate mixture while continuously mixing and heating the intermediate mixture to 75 degrees Celsius. Then, 238.39 gm of naphthenic acid and 26.49 g of capric acid mixture pre-heated at 76 degrees Celsius can be added to the intermediate mixture to form a combined mixture. The combined mixture temperature can then set to 110 degrees Celsius while agitating, and a low vacuum <0.1 cm Hg can be applied to the reactor. Water generated during the reaction can be removed and would expected to measure at least 14.94 gm (some water vapor escapes into the atmosphere). The reactor would be expected to contain less than 0.5% by weight of water after the reaction was completed and water removed. Diesel condensate can be fed back into the reactor. The reaction would be expected to complete in 35 minutes. Finally, add 49.01 gm of diesel #2 and 0.46 g of demulsifier can be added into the reactor to make a targeted 8 percent copper concentration in the reaction product. Example 18 would be expected to have a suitable initial viscosity of less than 400 cP and provide a clean reaction product with minimal, if any, residual solid materials left in the reactor after reaction completion.

Prophetic Example 19

Copper carboxylate can be synthesized by heating 91.88 g of diesel #2 at 75 degrees Celsius in the reactor. Then, 55.13 g of copper hydroxide (64 percent copper basis) can be added into the reactor to form an intermediate mixture while continuously mixing and heating the intermediate mixture to 75 degrees Celsius. Then, 158.39 gm of naphthenic acid and 105.95 g of capric acid mixture pre-heated at 76 degrees Celsius can be added to the intermediate mixture to form a combined mixture. The combined mixture temperature can then be set to 110 degrees Celsius while agitating, and a low vacuum <0.1 cm Hg can be applied to the reactor. Water generated during the reaction can be removed and would be expected to measure at least 14.94 gm (some water vapor escapes into the atmosphere). The reactor would be expected to contain less than 0.5% by weight of water after the reaction was completed and water removed. Diesel condensate can be fed back into the reactor. The reaction would be expected to be completed in 35 minutes. Finally, 49.01 gm of diesel #2 and 0.46 g of demulsifier can be added into the reactor to make a targeted 8 percent copper concentration in the reaction product. Example 19 would be expected to have a suitable initial viscosity of less than 400 cP and provide a clean reaction product with minimal, if any, residual solid materials left in the reactor after reaction completion.

Prophetic Example 20

Copper carboxylate can be synthesized by heating 91.88 g of diesel #2 at 75 degrees Celsius in the reactor. Then, 55.13 g of copper hydroxide (64 percent copper basis) can be added into the reactor to form an intermediate mixture while continuously mixing and heating the intermediate mixture to 75 degrees Celsius. Then, 268.88 g of capric acid mixture pre-heated at 76 degrees Celsius can be added to the intermediate mixture to form a combined mixture. The combined mixture temperature can then be set to 110 degrees Celsius while agitating, and a low vacuum <0.1 cm Hg can be applied to the reactor. Water generated during the reaction can be removed and would be expected to measure at least 14.94 gm (some water vapor escapes into the atmosphere). The reactor would be expected to contain less than 0.5% by weight of water after the reaction was completed and water removed. Diesel condensate can be fed back into the reactor. The reaction would be expected to complete in 35 minutes. Finally, 49.01 gm of diesel #2 and 0.46 g of demulsifier can be added into the reactor to make a targeted 8 percent copper concentration in the reaction product. Example 20 would be expected to have a suitable initial viscosity of less than 400 cP and provided a clean reaction product with minimal, if any, residual solid materials left in the reactor after reaction completion.

Prophetic Example 21

Copper carboxylate can be synthesized by heating 91.88 g of diesel #2 at 75 degrees Celsius in the reactor. Then, 55.13 g of copper hydroxide (64 percent copper basis) can be added into the reactor to form an intermediate mixture while continuously mixing and heating the intermediate mixture to 75 degrees Celsius. Then, 264.88 g of pelargonic acid preheated at 76 degrees Celsius can be added to the intermediate mixture to form a combined mixture. The combined mixture temperature can then be set to 110 degrees Celsius while agitating, and a low vacuum <0.1 cm Hg can be applied to the reactor. Water generated during the reaction can be removed and would be expected to measure at least 17.50 gm (some water vapor escapes into the atmosphere). The reactor would be expected to contain less than 0.5% by weight of water after the reaction was completed and water removed. Diesel condensate can be fed back into the reactor. The reaction would be expected to complete in 35 minutes. Finally, 49.01 gm of diesel #2 and 0.46 g of demulsifier can be added into the reactor to make a targeted 8 percent copper concentration in the reaction product. Example 21 would be expected to have a suitable initial viscosity of less than 400 cP and provide a clean reaction product with minimal, if any, residual solid materials left in the reactor after reaction completion.

Prophetic Example 22

Copper carboxylate can be synthesized by heating 91.88 g of diesel #2 at 75 degrees Celsius in the reactor. Then, 55.13 g of copper hydroxide (64 percent copper basis) can be added into the reactor to form an intermediate mixture while continuously mixing and heating the intermediate mixture to 75 degrees Celsius. Then, 264.88 g of capric acid pre-heated at 76 degrees Celsius can be added to the intermediate mixture to form a combined mixture. The combined mixture temperature can then be set to 110 degrees Celsius while agitating, and a low vacuum <0.1 cm Hg can be applied to the reactor. Water generated during the reaction can be removed and would be expected to measure at least 17 gm (some water vapor escapes into the atmosphere). The reactor would be expected to contain less than 0.5% by weight of water after the reaction was completed and water removed. Diesel condensate can be fed back into the reactor. The reaction would be expected to complete in 35 minutes. Finally, 49.01 gm of diesel #2 and 0.46 g of demulsifier can be added into the reactor to make a targeted 8 percent copper concentration in the reaction product. Example 22 would be expected to have a suitable initial viscosity of less than 400 cP and provide a clean reaction product with minimal, if any, residual solid materials left in the reactor after reaction completion.

It is believed that other methods according to the present disclosure can also reduce initial reaction viscosity, facilitate uniform agitations, reduced solid sediment, decrease reaction time, and/or increase reaction rate/yield.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited.

The grammatical articles "a," "an," and "the," as used herein, are intended to include "at least one" or "one or more," unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to,"

"related to," or other past-tense adjectives are generally not intended to exclude such variants, unless context dictates otherwise.

One skilled in the art will recognize that the herein-described components, devices, operations/actions, and objects, and the discussion accompanying them, are used as examples for the sake of conceptual clarity and that various configuration modifications are contemplated. Consequently, as used herein, the specific examples/embodiments set forth and the accompanying discussion are intended to be representative of their more general classes. In general, use of any specific exemplar is intended to be representative of its class, and the non-inclusion of specific components, devices, operations/actions, and objects should not be taken limiting. While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed and not as more narrowly defined by particular illustrative aspects provided herein.

What is claimed is:

1. A method for producing copper carboxylate, the method comprising:
    combining a hydrocarbon solvent and a copper compound to form an intermediate mixture, wherein the hydrocarbon solvent comprises a flash point in a range of 58 degrees Celsius to 140 degrees Celsius;
    heating a carboxylic acid having at least 8 carbon atoms to a temperature of at least 30 degrees Celsius to form a heated carboxylic acid; and
    combining the intermediate mixture and the heated carboxylic acid to form a reaction product comprising copper carboxylate, wherein an elemental copper concentration is in a range of 2 percent to 12 percent based on a total weight of the reaction product; and
        at least 20 percent by weight hydrocarbon solvent based on the total weight of the reaction product.

2. The method of claim 1, wherein the carboxylic acid comprises at least one of
    a formula of R—COOH or R—CO$_2$H, where R is an alkyl group, an alkenyl group, or an aryl group; or
    a formula of C$_n$H$_{2n-z}$O$_2$, where Z is 0, 2, 4, 6, or 8 and n is in a range of 8 to 20.

3. The method of claim 1, wherein the carboxylic acid is derived from petroleum.

4. The method of claim 1, wherein the carboxylic acid comprises an acid value in a range of 100 mg*KOH/g to 455 mg*KOH/g, a molecular weight in a range of 120 grams per mole to 700 grams per mole, a water content of less than 0.5 percent by total weight of the carboxylic acid, and a viscosity at 70 degrees Celsius in a range of 50 cP to 1500 cP.

5. The method of claim 1, wherein the carboxylic acid is naphthenic acid.

6. The method of claim 1, wherein the intermediate mixture is at a temperature in a range of 55 degrees Celsius to 90 degrees Celsius prior to combining with the heated carboxylic acid.

7. The method of claim 1, wherein the combining the intermediate mixture and the heated carboxylic acid forms a mixture with a viscosity of no greater than 2,500 cP at 25 degrees Celsius.

8. The method of claim 1 further comprising introducing a defoamer, a demulsifying agent, a biocide, or a combination thereof.

9. The method of claim 1, wherein the hydrocarbon solvent comprises diesel, fuel oil, pole-treating oil, a creosote-petroleum mixture, or a combination thereof.

10. The method of claim 1, wherein an elemental copper percentage in the copper compound is in a range of 55 percent to 65 percent by total weight of the copper compound.

11. The method of claim 1, wherein the copper compound comprises copper metal, copper (I) oxide, copper (II) oxide, copper hydroxide, copper carbonate, basic copper carbonate, copper oxychloride, or a combination thereof.

12. The method of claim 1, wherein a mean average particle size of the copper compound is in a range of 0.05 um to 500 um.

13. The method of claim 1, wherein a yield of the copper carboxylate is at least 90 percent.

14. The method of claim 1, wherein the copper carboxylate comprises copper naphthenate.

15. The method of claim 1, wherein the carboxylic acid is heated to a temperature in a range of 50 degrees Celsius to 150 degrees Celsius to form the heated carboxylic acid.

16. The method of claim 1, further comprising adding penflufen to the reaction product in a weight ratio of elemental copper: penflufen in a range of 5:1 to 250:1.

17. The method of claim 1, wherein the hydrocarbon solvent comprises diesel and the copper compound comprises copper hydroxide.

18. The method of claim 1, wherein the hydrocarbon solvent comprises a flash point in a range of 65 degrees Celsius to 100 degrees Celsius.

19. The method of claim 1, wherein the hydrocarbon solvent comprises a flash point in a range of 58 degrees Celsius to 76 degrees Celsius.

20. The method of claim 19, wherein the copper compound comprises copper hydroxide.

21. A method for producing copper naphthenate, the method comprising:
    combining a hydrocarbon solvent and a copper compound to form an intermediate mixture, wherein the intermediate mixture is at a temperature in a range of 50 degrees Celsius to 125 degrees Celsius, wherein the hydrocarbon solvent comprises a flash point in a range of 58 degrees Celsius to 140 degrees Celsius;
    heating naphthenic acid to a temperature in a range of 50 degrees Celsius to 150 degrees Celsius to form a heated naphthenic acid; and
    combining the intermediate mixture with the heated naphthenic acid to form a reaction product comprising copper naphthenate, wherein an elemental copper concentration is in a range of 2 percent to 12 percent based on a total weight of the reaction product; and
        at least 20 percent by weight hydrocarbon solvent based on the total weight of the reaction product.

22. The method of claim 21, wherein a weight ratio of carboxylic acid to copper compound is in a range of 3:1 to 10:1.

23. The method of claim 21, wherein the hydrocarbon solvent comprises diesel and the copper compound comprises copper hydroxide.

24. A wood preservative composition produced by the method of claim 1.

25. The wood preservative composition of claim 24, further comprising penflufen.

26. A wood product produced by treating the wood product with the wood preservative composition of claim 24.

27. The wood preservative composition of claim 25, wherein a weight ratio of elemental copper: penflufen is in a range of 5:1 to 250:1.

28. A wood product produced by treating the wood product with the wood preservative composition of claim 25, wherein a penflufen retention in the wood product is in a range of 0.004 kg/m$^3$ to 0.2 kg/m$^3$ and an elemental copper retention in the wood product is in a range of 0.5 kg/m$^3$ to 3.2 kg/m$^3$.

* * * * *